United States Patent [19]

Lunts et al.

[11] 4,000,193
[45] Dec. 28, 1976

[54] PHARMACOLOGICALLY ACTIVE COMPOUNDS

[75] Inventors: Lawrence Henry Charles Lunts; David Trevor Collin, both of London, England

[73] Assignee: Allen & Hanburys Limited, London, England

[22] Filed: May 6, 1974

[21] Appl. No.: 467,212

[30] Foreign Application Priority Data

May 7, 1973 United Kingdom ............ 21553/73

[52] U.S. Cl. .................. 260/559 S; 260/559 A
[51] Int. Cl.² ..................................... C07C 103/22
[58] Field of Search .................. 260/559 S, 559 A

[56] References Cited

UNITED STATES PATENTS

| 3,483,221 | 12/1969 | Wilhelm et al. | 260/326.14 T |
|---|---|---|---|
| 3,644,353 | 2/1972 | Lunts et al. | 260/559 S |
| 3,644,520 | 2/1972 | Hartley et al. | 260/559 |

FOREIGN PATENTS OR APPLICATIONS

| 6,919,614 | 7/1970 | Netherlands | 260/559 S |
|---|---|---|---|
| 1,260,521 | 1/1972 | United Kingdom | |
| 1,266,058 | 3/1972 | United Kingdom | |

OTHER PUBLICATIONS

Crowther et al., J. Med. Chem., vol. 11, pp. 1009–1013, (1968).
Howe et al., J. Med. Chem., vol. 11, pp. 1000–1008, (1968).
Grams et al., Jl. Farmeco Ed. Soc., vol. XXI, pp. 4–15, (1966).

*Primary Examiner*—C. Davis
*Attorney, Agent, or Firm*—Bacon & Thomas

[57] ABSTRACT

Compounds of the formula:

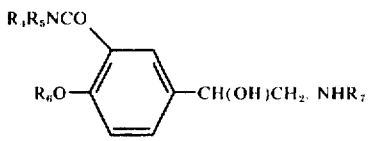

in which:
  $R_4$ and $R_5$ independently represent hydrogen or lowr alkyl;
  $R_6$ represents a straight or branched alkyl or alkenyl group containing from 4 to 6 carbon atoms, inclusive, or
  $R_6$ represents a straight or branched alkyl group containing from 2 to 6 carbon atoms, inclusive, which alkyl group is substituted by one or more hydroxy, alkoxy or acyloxy groups; or by an aryl group which may be substituted by one or more hydroxy, alkoxy or acyloxy groups as before; and
  $R_7$ represents a straight or branched alkyl group containing from 3 to 6 carbon atoms, inclusive, optionally substituted by an alkoxy group or by an aryl or aryloxy group which, alkoxy, aryl or aryloxy group may, in turn be substituted by hydroxy, alkoxy, acetamido or methanesulphonamido groups, and pharmaceutically acceptable salts thereof. These compounds have utility in the treatment of cardiovascular diseases.

9 Claims, No Drawings

PHARMACOLOGICALLY ACTIVE COMPOUNDS

This invention which is an improvement of that described in our U.K. Specification No. 1,260,521 relates to phenylethanolamine derivatives having useful biological activity and to compositions containing the same.

In our prior U.K. patent specification No. 1,260,521 there are disclosed and claimed compounds of the general formula:

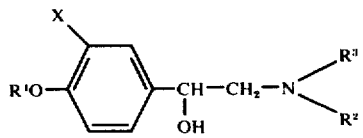

and physiologically acceptable acid addition salts, in which:

$R^1$ is a lower alkyl, lower alkenyl or arylalkyl radical, which radicals may optionally be substituted by one or more alkoxy or hydroxy groups;

$R^2$ represents a hydrogen atom or a lower alkyl radical which may optionally be substituted by one or more hydroxy groups, amino groups, or heterocyclic rings containing one or more heteroatoms or represents a cycloalkyl, arylalkyl or aryloxyalkyl radical, which radicals may optionally be substituted by one or more alkoxy or hydroxy groups;

$R^3$ represents a hydrogen atom or a benzyl group;

X represents a group of the formula $-CONR^4R^5$ where $R^4$ and $R^5$ which may be the same or different represent hydrogen or lower alkyl; with the proviso that when $R^2$ is tertiary butyl and $R^1$ is a benzyl group then $R^3$ represents a hydrogen atom.

It has now been found that certain compounds related to those of the above general formula show an unexpected selectivity in their pharmacological actions which makes their use in cardiovascular diseases, e.g. angina pectoris, hypertension or cardiac arrhythmias, especially advantageous.

The compounds of the main patent are non-selective blockers of β-adrenoreceptors at both $\beta_1$ and $\beta_2$ sites. The blockade of $\beta_2$-adrenoreceptors in the lungs may give rise to bronchospasm, and the use of substances with this property is contra-indicated in patients with asthma or bronchitis where lung function is impaired.

The compounds of the present invention surprisingly show high potency in blocking adrenergic responses selectively at $\beta_1$ receptors, e.g. those in the heart, with minimal effects on $\beta_2$ receptors of the lung. They may therefore be used advantageously in patients with pulmonary disorders to avoid unwanted side-effects.

The invention therefore provides compounds of the general formula:

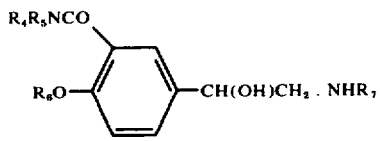

in which:

$R_4$ and $R_5$ independently represent hydrogen or lower alkyl;

$R_6$ represents a straight or branched alkyl or alkenyl group containing from 4 to 6 carbon atoms, inclusive, or $R_6$ represents a straight or branched alkyl group containing from 2 to 6 carbon atoms, inclusive, which alkyl group is substituted by one or more hydroxy, alkoxy or acyloxy groups; or by an aryl group which may be substituted by one or more hydroxy, alkoxy or acyloxy groups as before; and $R_7$ represents a straight or branched alkyl group containing from 3 to 6 carbon atoms, inclusive, optionally substituted by an alkoxy group or by an aryl or aryloxy group which, alkoxy, aryl or aryloxy group may, in turn, be substituted by hydroxy, alkoxy, acetamido or methane sulphonamido groups, and pharmaceutically acceptable salts thereof.

Suitable salts of the compounds of formula I include salts with organic or inorganic acids containing pharmaceutically acceptable anions, e.g. hydrochloric, maleic acid, etc.

A particular class of compounds according to the invention are those in which $R_4$ and $R_5$ are both hydrogen. Preferably the group $R_6$ represents, within the definitions given above, one of the following groups:

$C_{4-6}$ alkyl, dihydroxyalkyl, hydroxyalkyl, alkoxyalkyl, acyloxyalkyl, aralkyl, hydroxyaralkyl, alkoxyaralkyl, acyloxyaralkyl, or alkenyl and the group $R_7$ preferably represents one of the following groups: alkyl, alkoxyalkyl, aralkyl, hydroxyaralkyl, mono and dialkoxyaralkyl, alkoxy-hydroxyaralkyl, acetamidoaralkyl, sulphonamidoaralkyl, aryloxyalkyl.

A particularly preferred class of compounds according to the invention are those in which $R_4$ and $R_5$ are both hydrogen and preferably the group $R_6$ represents one of the following groups:- 2-methoxyethyl, 2-ethoxyethyl, 2-propoxyethyl, 2isopropoxyethyl, 2-butoxyethyl, 2-hydroxyethyl, 2-acetoxyethyl, 2-phenethyl, 3-methoxypropyl, 3-ethoxypropyl, 3-hydroxypropyl, 2,3-dihydroxypropyl, butyl, 4-hydroxybutyl, 2-methylbutyl, 3-methylbutyl, 2-butenyl, pentyl, hexyl, and $R_7$ preferably represents isopropyl, 1-methylpropyl, 1-ethylpropyl, 1,2-dimethylpropyl, tertiarybutyl, 3-methoxy-1-methylpropyl, 3-ethoxy-1-methylpropyl, 2-methoxy-1-methylethyl, 4-methoxy-1-methylbutyl, 1-methyl-3-phenylpropyl, 3(4'-hydroxyphenyl)-1-methylpropyl, 3(3',4'-dimethoxyphenyl)-1-methylpropyl, 1-methyl-3-(4'-methoxyphenyl)propyl, 3-(4'-hydroxy-3'-methoxyphenyl)-1-methylpropyl, 2-methyl-3-phenylpropyl, 1,1-dimethyl-3-phenylpropyl, 3-(4'-acetamidophenyl)-1-methylpropyl, 3-(4'-methane sulphonamidophenyl)-1-methylpropyl, 3-phenylpropyl, 1-ethyl-3-phenylpropyl, 1-methyl-3-phenylbutyl, 1-methyl-2-phenoxyethyl.

As the compounds of general formula I possess at least one asymmetric carbon atom, the invention also includes all the possible optically active forms and racemic mixtures of the compounds. Racemic compounds may be resolved by conventional methods, for example by salt formation with an optically active acid, followed by fractional crystallisation.

Mixtures of racemic compounds may be separated by fractional crystallisation of the bases or their acid addition salts.

The selective blockade of $\beta_1$ adrenoreceptors was demonstrated in the anaesthetized dog by the reduction of the tachycardia induced by isoprenaline, while at the same time having little effect on the lowering of blood pressure induced by isoprenaline.

The results given below show that, unlike propranolol the standard non-selective β-blocker used in the treatment of angina and hypertension, the compounds of the invention, such as 2-(2-ethoxyethoxy)-5-[1-hydroxy-2-[(1-methyl-3-phenylpropyl) amine] ethyl] benzamide hydrochloride (Example 13) and 2-(2-ethoxyethoxy)-5-[1-hydroxy-2-[[3-(4-hydroxyphenyl)-1-methylpropyl]amino]ethyl] benzamide hydrochloride (Example 19) block the $β_1$ receptors in the heart, but not the $β_2$ receptors in peripheral circulation which includes airways smooth muscle.

|  | Equipotent dose relative to propranolol to produce β blockade | |
| --- | --- | --- |
|  | $β_1$ Heart Rate | $β_2$ Blood Pressure |
| Propranolol | 1.00 | 1.00 |
| Example 13 | 0.6 | 100 |
| Example 19 | 0.8 | 97 |

Thus the compounds of the invention have the advantage of being effective in the treatment of angina and hypertension while being less likely to induce bronchospasm.

The compounds may be formulated for use in human or veterinary medicine for therapeutic or prophylactic purposes. The invention therefore includes within its scope pharmaceutical compositions comprising as active ingredient compounds of general formula I or physiologically acceptable acid addition salts thereof. Preferred salts include the hydrochloride, sulphate, maleate, acetate, fumarate, lactate, and citrate. Such compositions may be presented for use in a conventional manner with the aid of carriers or excipients and formulatory agents as required, and with or without supplementary medicinal agents. These compositions include, for instance, solid or liquid preparations for oral use, suppositories and injections. Oral administration is most convenient in the form of tablets which may be prepared according to conventional methods and may be coated if desired. Injections may be formulated with the aid of physiologically acceptable carriers and agents as solutions, suspensions, or as dry products for reconstitution before use. The doses of the active ingredient which may be used may vary generally within the range of 5 mg to 1000 mg, preferably 20 mg to 200 mg.

The compounds according to the present invention may be made by processes analogous to those described in the parent patent.

A particularly preferred process consists of in the catalytic hydrogenation of the ether of formula (II):

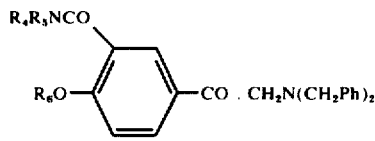

(II)

(in which $R_4$, $R_5$ and $R_6$ have the meanings given above) in the presence of a carbonyl compound e.g. an aldehyde or ketone yielding a group $R_7$. This catalytic hydrogenation is preferably effected in the presence of a supported noble metal catalyst such as palladium-charcoal or platinum-charcoal catalysts, or mixtures of these in a solvent with warming if necessary. This process involves hydrogenolysis of the benzyl groups, reductive alkylation of the so-formed primary amine, and reduction of the keto groups. One may also use as starting material the potential intermediates in this process that is to say the corresponding primary amine or the corresponding hydroxy dibenzylamino compound or the hydroxy primary amine. The ether (II) is preferably prepared by the alkylation of the parent ketone (III):

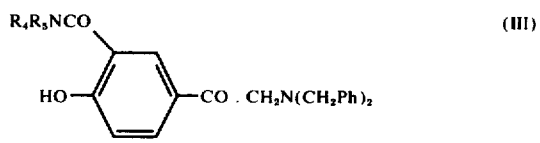

(III)

in which $R_4$ and $R_5$ have the above-stated meanings. Alkylation may be effected by standard procedures using an alkylating agent $R_6W$ in which $R_6$ has the meaning given above or is a group convertible thereto, for example a moiety with a protected hydroxy group and W may be for example a halogen atom or a tosyl group. The alkylation is preferably effected in a solvent in the presence of a base such as potassium carbonate or sodium hydride if necessary with heating. If desired, the sequence of the above reactions may be reversed and compounds of formula (I) may be prepared by the alkylation of corresponding phenols (I; $R_6$=H) by the methods before described.

Other methods which may be used are described in the main patent. Such methods include in particular the reduction of the ketone of the formula (IV):

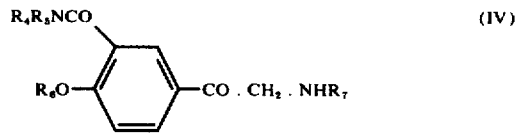

(IV)

This compound may be made by condensation of the haloketone (V)

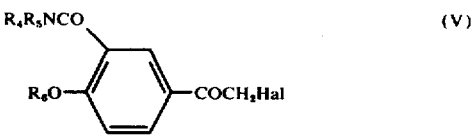

(V)

with an amine $R_7NH_2$. When an optically active amine is used, reduction of the resulting ketone yields a mixture of two diastereoisomers, which may be separated as the base or as a salt, by for example, fractional crystallisation.

In the above processes the group -$CONR_4R_5$ may be present in the starting material or may be formed at any convenient stage from an alkoxycarbonyl group -$COOR_8$, where $R_8$ represent an alkyl group by reaction with an amine $HNR_4R_5$ (in the simplest case, ammonia).

The following Examples illustrate the invention:

EXAMPLES 1–12

1.
5-[1-Hydroxy-2-[(1-methyl-3-phenylpropyl)amino]ethyl]-2-(pentyloxy)benzamide, hydrochloride a. 5-(N,N-Dibenzylglycyl)-2-(pentyloxy)benzamide

A solution of 5-(N,N-dibenzylglycyl)salicylamide (7.48 g) in dimethylformamide (75 ml) was added dropwise to a stirred suspension of sodium hydride (0.48 g) in dimethylformamide (25 ml). When hydrogen evolution ceased 1-bromopentane (3.0 g) was added. The mixture was heated at 100° for 2 hours and the dimethylformamide evaporated under reduced pressure leaving a brown gum which was washed with water (100 ml) and partitioned between water and ethyl acetate. The organic layer was dried (MgSO₄) and passed through a column of chromatographic neutral alumina (200 g) to remove the starting salicylamide. The ethyl acetate eluate was evaporated to leave a clear oil (7.0 g) which on trituration with light petroleum (b.p. 40°–60°) gave the pentyl ether as a white solid (6.6 g) m.p. 95°–97°. A portion was recrystallised from isopropanol to yield colourless needles, m.p. 98°–99°.

The following compounds were prepared in a similar manner from 5-(N,N-dibenzylglycyl)salicylamide using the alkylating agent quoted in brackets.

2(a) 2-Butyloxy-5-(N,N-dibenzylglycyl)benzamide, m.p. 136°–138°, 65% (Butyl bromide)

3(a) 5-(N,N-dibenzylglycyl)-2-hexyloxybenzamide, m.p. 92°–94°, 53% (hexyl iodide).

4(a) 5-(N,N-dibenzylglycyl)-2-(3-methylbutyloxy)-benzamide m.p. 114°–116°, 45% (3-methylbutyl p-toluenesulphonate).

5(a) 5-(N,N-dibenzylglycyl)-2-(2-methylbutyloxy)-benzamide, m.p. 117°–118°, 39% (2-methylbutyl p-toluenesulphonate).

6(a) 5-(N,N-dibenzylglycyl)-2-(2-hydroxyethoxy)-benzamide, m.p. 148°–151° (2-bromoethanol).

7(a) 5-(N,N-dibenzylglycyl)-2-(2-methoxyethoxy)-benzamide, m.p. 165°–168°, 81% (2-methoxyethyl p-toluene sulphonate).

8(a) 5-(N,N-dibenzylglycyl)-2-(3-methoxypropoxy)-benzamide, m.p. 107°–109°, 47% (3-methoxypropyl p-toluenesulphonate)

9(a) 5-(N,N-dibenzylglycyl)-2-(2-propoxyethoxy)-benzamide, m.p. 125°–127°, 26% (2-propoxyethyl p-toluenesulphonate), 10(a) 5-(N,N-dibenzylglycyl)-2-(2-isopropoxyethoxy) benzamide, m.p. 138°–139°, 37% (2-isopropoxyethyl, p-toluenesulphonate).

11(a) 2(2-butoxyethoxy)-5-(N,N-dibenzyglycyl)-benzamide, m.p. 111°–112°, 62% (2-butoxyethyl p-toluenesulphonate).

12(a) 5-(N,N-dibenzylglycyl)-2-(2-ethoxypropoxy)-benzamide, m.p. 113°–115°, 32% (2-ethoxypropyl p-toluenesulphonate)

1 b.
5-[1-Hydroxy-2-[(1-methyl-3-phenylpropyl)amino]ethyl]-2-(pentyloxy)benzamide hydrochloride.

5-(N,N-Dibenzylglycyl)-2-(pentyloxy)benzamide (4.0 g) and benzyl acetone (14 g) in ethanol (200 ml) containing acetic acid (0.45 g) were stirred with 5% platinum on carbon (0.5 g), pre-reduced 10% palladium on carbon (0.5 g), and hydrogen, at room temperature and atmospheric pressure. Hydrogen uptake (870 ml) was complete within 18 hours. The catalyst and solvent were removed and the residual oil in ethyl acetate (100 ml) was treated with ethereal hydrogen chloride to give the hydrochloride as colourless microcrystals (3.3 g) m.p. 178°–179° from methanol-ethyl acetate.

The following compounds 2–12 were prepared in a similar way from the corresponding ether described in Examples 2(a)–12(a)

2. 2-Butyloxy-5-[1-hydroxy-2-[(1-methyl-3-phenylpropyl) amino]ethyl]benzamide, hydrochloride, m.p. 158°–163°, 43%;

3. 5-[1-hydroxy-2-[(1-methyl-3-phenylpropyl)amino]ethyl]-2-hexyloxybenzamide, hydrochloride, m.p. 177°–178°, 82%;

4. 5-[1-hydroxy-2-[(1-methyl-3-phenylpropyl)amino]ethyl]-2-(3-methylbutyloxybenzamide, hydrochloride, m.p. 167°–177°, 84%;

5. 5-[1-hydroxy-2-[(1-methyl-3-phenylpropyl)amino]ethyl]-2-(2-methylbutoxy)benzamide, hydrochloride, m.p. 162°–170°, 84%;

6. 5-[1-hydroxy-2-[(1-methyl-3-phenylpropyl)amino]ethyl]-2-(2-hydroxyethoxy)benzamide, hydrochloride, m.p. 116°–118°, 43%.

7. 5-[1-hydroxy-2-[(1-methyl-3-phenylpropyl)amino]ethyl]-2-(2-methoxyethoxy)benzamide, hydrochloride, m.p. 136°–153°, 81%.

8. 5-[1-hydroxy-2-[(1-methyl-3-phenylpropyl)amino]ethyl]-2-(3-methoxypropoxy)benzamide, hydrochloride, m.p. 138°–140°, 80%;

9. 5-[1-hydroxy-2-[(1-methyl-3-phenylpropyl)amino]ethyl]-2-(2-propoxyethoxy)benzamide, m.p. 96°–102°, 35%;

10. 5-[1-hydroxy-2-[(1-methyl-3-phenylpropyl)amino]ethyl]-2-(isopropoxyethoxy)benzamide, hydrochloride, m.p. 157°–159°, 54%.

11. 2-(2-butyloxyethoxy)-5-[1-hydroxy-2-[(1-methyl-3-phenylpropyl)amino]ethyl]benzamide, hydrochloride, m.p. 122°–123°, 65%.

12. 5-[1-hydroxy-2-[(1-methyl-3-phenylpropyl)-amino]ethyl]-2-(2-ethoxypropoxy)benzamide, m.p. 138°–144°, 75%.

EXAMPLE 13

2-(2-Ethoxyethoxy)-5-[1-hydroxy-2-[(1-methyl-3-phenylpropyl)amino]ethyl]benzamide, hydrochloride

Method A a. 5-(N,N-Dibenzylglycyl)-2-(2-ethoxyethoxy)benzamide

A mixture of N,N-dibenzylglycyl salicylamide (935 g), 2-ethoxyethyl-p-toluenesulphonate (730 g), anhydrous potassium carbonate (350 g) in butanone (7.5 l) was stirred and heated at reflux for 27 hours. The hot mixture was filtered to remove the inorganic salts and the filtrate was concentrated to about 2.4 l and the crude product allowed to crystallise. This was filtered off, washed with butanone and dried. This solid was dissolved in hot ethyl acetate (4.1 ) and the hot solution filtered to remove insoluble material. The required product crystallised on cooling and was filtered off, washed with ethyl acetate and dried. It had m.p. 128°–131°.

b.
2-(2-Ethoxyethoxy)-5-[1-hydroxy-2-[(1-methyl-3-phenylpropyl)amino]ethyl]benzamide, hydrochloride.

A mixture of 5-(N,N-dibenzylglycyl)-2-(2-ethoxyethoxy)benzamide (11.15 g) benzylacetone (4.45 g), glacial acetic acid (1.7 ml), ethanol (55 ml), 10% palladium oxide on carbon (1 g) and 5% platinum on carbon (1 g) was stirred at 40° in an atmosphere of hydrogen until 2.5 l of hydrogen had been absorbed. The catalyst was then removed by filtration and the filtrate was evaporated to a volume of about 20 ml. Ether (60 ml) was added followed by 10% hydrogen chloride in ethanol (10 ml). The crude hydrochloride crystallised on cooling and was filtered off, and dried (9.3 g) m.p. 141°. This was recrystallised from ethanol-ether. The solid was filtered off and dried to give 2-(2-ethoxyethoxy)-5-[1-hydroxy-2-[(1-methyl-3-phenylpropyl)amino]ethyl]benzamide, hydrochloride (8.8 g) m.p. 142°.

Method B

A mixture of 5-[1-hydroxy-2-[(1-methyl-3-phenylpropyl)-amino]ethyl]salicylamide (3.3 g) (described in British Pat. No. 1,266,058), 2-ethoxyethyl-p-toluenesulphonate (3.0 g), anhydrous potassium carbonate (1.5 g) and dimethylformamide (50 ml) was stirred and heated at 50° for 17 hours. The solvent was distilled off in vacuo and the residue treated with water (25 ml) and ethyl acetate (25 ml). The ethyl acetate layer was separated and washed with water (25 ml), N sodium hydroxide (25 ml) and water (25 ml). The ethyl acetate was evaporated in vacuo. The residue was dissolved in ethanol (10 ml) and ether (50 ml) was added, followed by 10% hydrogen chloride in ethanol (3 ml). The precipitate was filtered off and dried to give the crude product (1.9 g) m.p. 139°–141°. This was recrystallised from ethanol-ether to give 2-(2-ethoxyethoxy)-5-[1-hydroxy-2-[(1-methyl-3-phenylpropyl)amino]ethyl]-benzamide, hydrochloride (1.6 g) m.p. 141°. An nmr spectrum of a 12.5% solution in pyridine, containing 12.5% concentrated hydrochloric acid, at 90° C exhibited two pairs of doublets centred at 8.30 τ, and 8.31 τ.

METHOD C 2-(2-Ethoxyethoxy)-5-[1-hydroxy-2-[(1-methyl-3-phenylpropyl)-amino]ethyl]benzamide hydrochloride A solution of 5-bromoacetyl-2-(2-ethoxyethoxy)benzamide (0.33 g), 1-methyl-3-phenylpropylamine (0.15 g) and triethylamine (0.1 g) in dry ethanol (30 ml) was refluxed for 4 hours. An excess of sodium borohydride was added to the cooled mixture and, when effervescence had ceased, the solvent was removed under reduced pressure. The residue was acidified with 2N hydrochloric acid and shaken with ethyl acetate (3 × 15 ml). The aqueous solution was basified with sodium hydroxide, extracted with ethyl acetate (3 × 15 ml) and evaporated to a viscous gum (0.37 g). This was washed with ether dissolved in ethyl acetate and treated with hydrogen chloride in ether to form the hydrochloride (0.3 g), m.p. 141°–142°.

EXAMPLE 14

The separation of the two racemic forms of 2-(2-ethoxyethoxy)-5-[1-hydroxy-2-[(-1-methyl-3-phenylpropyl)amino]ethyl]benzamide[produced according to Example 13 Method B]

a. Racemate 1

2-(2-Ethoxyethoxy)-5[1-hydroxy-2-[(1-methyl-3-phenylpropyl)amino]ethyl]benzamide, (25 g) was treated with dilute ammonia to give the free base m.p. 110°–119°. This was recrystallised eight times from ethyl acetate to give a solid of constant m.p. 128°–130° (5.3 g). This was dissolved in ethanol (17 ml) and treated with 10% hydrogen chloride in ethanol (6 ml) followed by hot ethyl acetate (75 ml). The precipitate was filtered off and recrystallised twice from a 10% solution in ethanol to give the hydrochloride of Racemate I (1.85 g) m.p. 138°–140°. The nmr spectrum in pyridine containing 12.5% hydrochloric acid at 90° C showed a doublet centred at 8.3τ.

b. Racemate 2

2-(2-Ethoxyethoxy)-5-[1-hydroxy-2-[(1-methyl-3-phenylpropyl)amino]ethyl]benzamide, hydrochloride, m.p. 140°–141° (25 g) was recrystallised ten times from ethanol (10% w/v) to give the hydrochloride of Racemate 2, (2.5 g) as a solid of constant m.p. 163°–166°. The nmr spectrum in pyridine containing 12.5% hydrochloric acid showed a doublet centred at 8.31τ.

EXAMPLE 15

5-[1-Hydroxy-2[(1-methyl-3-phenylpropyl)amino]ethyl]-2-(3-hydroxypropoxy)benzamide, hydrochloride a.
5-(N,N-Dibenzylglycyl)-2-(3-hydroxypropoxy)benzamide

A mixture of 5-(N,N-dibenzylglycyl)salicylamide (10.0 g), sodium iodide (4.0 g), potassium carbonate (3.7 g) and 3-chloropropan-1-ol (2.56 g) in butanone (100 ml) was heated under reflux for 24 hours, and filtered to give a cream solid (15.3 g). This was extracted with boiling ethanol and the clear solution was cooled to give a yellow solid (4.0 g) which was crystallised from methanol as colourless crystals (3.4 g). It had m.p. 171°–175°.

b.
5-[1-Hydroxy-2-[(1-methyl-3-phenylpropyl)amino]ethyl]- 2-(3-hydroxypropoxy)benzamide, hydrochloride A mixture of 5-(N,N-dibenzylglycyl)-2-(3-hydroxypropoxy)benzamide (2.0 g), benzylacetone (0.68 g), ethanol (150 ml) and acetic acid (0.28 g) was stirred in the presence of 5% palladium of kieselguhr (0.6 g) and 5% platinum on carbon (0.3 g) under hydrogen at atmospheric pressure. The temperature was maintained at 45° for the first 5 hours after which time the reaction was carried out at room temperature. Uptake of hydrogen (635 ml) was complete within 72 hours. After removal of catalysts, the solution was treated with ethereal hydrogen chloride and evaporated to yield a gummy solid. This was triturated with dry ether to give the hydrochloride as a colourless, friable solid (1.85 g) which started to decompose above 60°.

EXAMPLE 16

2-(2,3-Dihydroxypropoxy)-5-[1-hydroxy-2-[(1-methyl-3-phenylpropyl)amino]ethyl]benzamide, hydrochloride a.

5-(N,N-Dibenzylglycyl)-2-(2,3-dihydroxypropoxy)-benzamide

3-Chloropropane-1,2-diol (2.65 g) was added to a refluxing suspension of 5-(N,N-dibenzylglycyl)salicylamide sodium salt (10.0 g) in toluene (100 ml) and heating was continued for 6 hours. The mixture was cooled and filtered and the filtrate was evaporated. The residue was crystallised twice from ethanol to give the required product m.p. 169°–173°.

b.

2-(2,3-Dihydroxypropoxy-5-[1-hydroxy-2-[(1-methyl-3-phenylpropyl)amino]ethyl]benzamide, hydrochloride A mixture of 5-(N,N-dibenzylglycyl)-2-(2,3-dihydroxypropoxy)benzamide (2.0g), benzyl acetone (0.74 g), acetic acid (0.3 g) and ethanol (150 ml) was stirred in the presence of 10% palladium on carbon (0.3 g) and 5% platinum on carbon (0.3 g) under hydrogen at atmospheric pressure. Uptake of hydrogen (538 ml) was complete within 70 hours. After removal of catalysts the solution was treated with ethereal hydrogen chloride and evaporated to yield a gummy solid. This was triturated with dry ether to give the hydrochloride as a colourless, friable solid (1.15 g) which decomposed above 56°.

EXAMPLE 17

2-(4-Hydroxybutoxy)-5-[1-hydroxy-2-[(1-methyl-3-phenylpropyl)amino]ethyl]benzamide, anisate a.

5-(N,N-Dibenzylglycyl)-2-(4-tetrahydropyranyloxybutoxy)benzamide

A mixture of 5-(N,N-dibenzylglycyl)salicylamide, sodium salt (3.96 g), 2-(4-chlorobutoxy)tetrahydropyran (1.92 g) sodium iodide (1.40 g) and butanone (100 ml) was heated under reflux for 30 hours and filtered. The filtrate was evaporated to give an oil which crystallised from isopropanol to afford the ether as colourless crystals (2.95 g), m.p. 118°–123°.

b.

5-(N,N-Dibenzylglycyl)-2-(4-hydroxybutoxy)benzamide 5-(N,N-Dibenzylglycyl)-2-(4-tetrahydropyranyloxybutoxy) benzamide (5.0 g) in methanol (100 ml) and a 1M aqueous solution of oxalic acid (75 ml) was allowed to stand at room temperature for 2 hours and basified with sodium hydrogen carbonate. The methanol was removed under reduced pressure and the aqueous suspension was extracted with ethyl acetate. The dried extracts were evaporated to give the product (3.3g) m.p. 128.5° – 132°. (from ethyl acetate).

c.

2-(4-Hydroxybutoxy)-5-[1-hydroxy-2-[(1-methyl-3-phenylpropyl)amino]ethyl]benzamide, anisate A mixture of 2-(4-hydroxybutoxy)-5-[1-hydroxy-2-[(1-methyl-3-phenylpropyl)amino]ethyl]benzamide anisate (2.6 g), benzyl acetate and ethanol (150 ml) was stirred in the presence of 10% palladium on carbon (0.3 g) and 5% platinum on carbon (0.3 g) under hydrogen at atmospheric pressure. Hydrogen uptake (563 ml) was complete within 18 hours. The solvent and catalysts were removed to afford a colourless oil which was treated with an ethanolic solution of anisic acid. The solvent was removed and the gum was triturated with dry ether to yield the anisate (0.5 g).

EXAMPLE 18

2-(2-Ethoxyethoxy)-5-[1-hydroxy-2-[(1-ethylpropyl)amino]ethyl]benzamide, fumarate A mixture of 2-(2-ethoxyethoxy)-5-dibenzylglycyl benzamide (4.4 g) and diethyl ketone (2.95 g) in ethanol (300 ml) was hydrogenated in the presence of 5% platinum oxide on carbon (0.5 g) and 10% palladium oxide on carbon (0.6 g) until the theoretical amount of hydrogen (0.04 mole) had been absorbed. The catalyst and solvent were removed and the residue was converted into a fumarate salt, m.p. 132°–135° (from methanol-ethyl acetate).

The following compounds were prepared in a similar manner by the reductive alkylation of 2-(ethoxyethoxy)-5-dibenzylglycyl benzamide with the appropriate carbonyl compound in brackets. 19. 2-(2-ethoxyethoxy)-5-[1-hydroxy 2-[[3-(4-hydroxyphenyl)-1-methylpropyl]amino]ethyl]benzamide, hydrochloride].

20. 2-(2-Ethoxyethoxy)-5-[1-hydroxy-2-[[3-phenylpropyl]amino]ethyl]benzamide, m.p. 156°–158°, [3-phenylpropionaldehyde].

21. 2-(2-Ethoxyethoxy)-5-[2-[(1-ethyl-3-phenylpropyl)amino]-1-hydroxyethyl]benzamide, m.p. 94–98° [1-phenylpentan-3-one]

22. 2-(2-Ethoxyethoxy)-5-[1-hydroxy-2-[(1-methyl-4-phenylbutyl)amino]ethyl]benzamide, hydrochloride, m.p. 170°–174° [1-phenylpentan4-one].

23. 2-(2-Ethoxyethoxy)-5-[2-[(3-(3,4-dimethoxyphenyl-1-methylpropyl)amino]-1-hydroxyethyl]benzamide, hydrochloride, m.p. 135°–152° [3,4-dimethoxybenzyl acetone].

24. 2-(2-Ethoxyethoxy)-5-[1-hydroxy-2-[isopropylamino]ethyl]benzamide, hydrochloride, m.p. 168.5°–170° [acetone].

25. 2-(2-Ethoxyethoxy)-5-[1-hydroxy-2-[(1-methyl-2-phenoxyethyl)amino]ethyl]benzamide, hydrochloride, m.p. 131°. (phenoxyacetone).

26. 2-(2-Ethoxyethoxy)-5-[1-hydroxy-2-[(1-methylbutylamino]ethyl]-benzamide, hydrochloride, m.p. 112°–114° (pentan-2-one).

27. 2-(2-Ethoxyethoxy)-5-[1-hydroxy-2-[(1,2-dimethylpropyl)amino]ethyl]benzamide, hydrochloride, m.p. 72°–73° (3-methyl-butan-2-one).

28. 2-(Ethoxyethoxy)-5-[1-hydroxy-2[[3-(4-hydroxy-3-methoxyphenyl)-1-methylpropyl]amino]ethyl]benzamide, hydrochloride, m.p. 128°–132° (4-hydroxy-3-methoxybenzyl acetone).

29. 2-(Ethoxyethoxy)-5-[1-hydroxy-2-[[3-(4-methoxyphenyl)-1-methylpropyl]-amino]ethyl]benzamide, m.p. 85°–87° (4-methoxybenzyl acetone).

EXAMPLE 30

2-(2-Ethoxyethoxy)-5-[1-hydroxy-2-[(2-methyl-3-phenylpropyl) amino]ethyl]benzamide, citrate salt, dihydrate 5-(N,N-Dibenzylglycyl)-2-(2-ethoxyethoxy)benzamide (3.35 g) was hydrogenated in ethanol (200 ml) at room temperature and atmospheric pressure in the presence of 5% platinum on carbon (0.4 g) and 10% palladium on carbon (0.4 g). Hydrogen uptake (598 ml) was complete after 46 hr. The catalysts were removed and α-methylcinnamaldehyde (1.2 g) was added to the solution, which was then heated at 60° for 45 min. The solution was hydrogenated again using 5% platinum on carbon (0.4 g) and 10% palladium on carbon (0.4 g), for 4.5 hours when hydrogen uptake was complete (481 ml). The catalysts and solvent were removed and the resulting oil was converted into its citrate salt (2.55 g) m.p. 65°–80°.

EXAMPLE 31

2-(2-Ethoxyethoxy)-5-[1-hydroxy-2-[(1-methylpropyl)amino]ethyl]benzamide, p-amino-benzoate salt, monohydrate 5-(N,N-Dibenzylglycyl)-2-(2-ethoxyethoxy)benzamide (3.55 g) was hydrogenated in the presence of 5% platinum on carbon (0.4 g) and 10% palladium on carbon (0.4 g) in ethanol (200 ml), containing 4-acetoxy-2-butanone (1.04 g). Hydrogen uptake (1002 ml) was complete after 70 hours. The catalysts and solvent were removed and the oil was converted into its p-aminobenzoate salt which decomposed above 50°. Equiv. wt. Found 246; requires 240.

EXAMPLE 32

2-(2-Ethoxyethoxy)-5-[1-hydroxy-2-[(1-methyl-3-phenylpropyl)amino]ethyl]-N-methylbenzamide a. 5-(N,N-Dibenzylglycyl)-2-(2-ethoxyethoxy)benzoic acid, methyl ester A solution of methyl-5-(N,N-dibenzylglycyl) salicylate, hydrochloride (21.3 g) (prepared according to British Pat. No. 1,200,886) in dry dimethylformamide (300 ml) was added dropwise with stirring to a suspension of sodium hydride (2.4 g) in dimethylformamide (200 ml). After cessation of hydrogen evolution, 2-ethoxyethyl-p-toluene sulphonate (12.8 g) was added dropwise and the mixture heated at 100° for 40 hours. The dimethylformamide was removed in vacuo and the residue partitioned between water (200 ml) and ethyl acetate (200 ml). The organic phase was dried (MgSO₄) and evaporated to give an oil (18.9 g) which was chromatographed on alumina (Type 'H'; 250 g). Elution with ethyl acetate gave the glycyl compound (8 g), which was converted into a hydrochloride salt, m.p. 57° (from methanol-ether).

b. 2-(2-Ethoxyethoxy)-5-[1-hydroxy-2-[(1-methyl-3-phenylpropyl)amino]ethyl]benzoic acid, methyl ester A solution of methyl 5-(N,N-dibenzylglycyl)-2-(2-ethoxyethoxy)benzoate (6.1 g) in ethanol (300 ml) was reductively alkylated with benzyl acetone (1.95 g) and hydrogen in the presence of 5% platinum on carbon (0.8 g) and 10% palladium on Kieselguhr (1.2 g). When the uptake of hydrogen (1175 ml) ceased the catalyst and solvents were removed to afford an oil (6 g). This was dissolved in ether (150 ml) and extracted with dilute hydrochloric acid. The extracts were basified with 2N sodium bicarbonate solution and extracted with ether. The organic extracts were dried to give the ether as an oil (2.4 g). A portion was converted into an anisate salt with anisic acid in ether to give a white solid m.p. 100°–101°.

c. 2-(2-Ethoxyethoxy)-5-[1-hydroxy-2-[(1-methyl-3-phenylpropyl)amino]ethyl]-N-methylbenzamide A solution of 2-(2-ethoxyethoxy)-5-[1-hydroxy-2-[(1-methyl-3-phenylpropyl)amino]ethyl]benzoic acid, methyl ester (0.9 g) in 30% ethanolic methylamine (40 ml) was allowed to stand at room temperature for 11 days and then evaporated to dryness. The residue was triturated with ethyl acetate at 0° to give the methylamide as a colourless powder, m.p. 124°–126.5°.

EXAMPLE 33

2-(2-Butenyloxy)-5-[1-hydroxy-2-[(1-methyl-3-phenylpropyl)amino]ethyl]benzamide, hydrochloride A solution of sodium ethoxide from sodium (1.84 g) in ethanol (50 ml) was added to a suspension of 5-[1-hydroxy2-[(1-methyl-3-phenylpropyl)amino]ethyl]-salicylamide (12 g) in ethanol (200 ml). The mixture was heated under reflux and treated over a period of 2 hours with a solution of crotyl bromide (5.1 g) in ethanol (100 ml). After a further 3 hours at reflux the mixture was evaporated and the residue dissolved in ethyl acetate (75 ml) and water (75 ml). The ethyl acetate solution was extracted with 2N sodium hydroxide solution (50 ml), filtered, dried and evaporated, to afford the base as a yellow solid that recrystallised from ethyl acetate as colourless crystals (2.15 g), m.p. 106°–110°. The hydrochloride, m.p. 120°–134°, was obtained by treatment of an ethanolic solution of the base with ethereal hydrogen chloride.

EXAMPLE 34

5-[1-Hydroxy-2-[(1-methyl-3-phenylpropyl)amino]ethyl-2-(2-phenylethoxy)benzamide.

A mixture of 5-[1-hydroxy-2-[(1-methyl-2-phenylpropyl)amino]ethyl]salicylamide (8.7 g), potassium carbonate (3.6 g) and phenethyl bromide (6 g) in butanone (200 ml) was stirred and heated under reflux for 100 hours. The cooled mixture was filtered, the filtrate was evaporated and the residual oil dissolved in ethyl acetate (200 ml) and water (200 ml). The aqueous solution was re-extracted with ethyl acetate (3 × 100 ml) and the dried organic solutions were concentrated to a small volume (30 ml) and passed down a column of chromatograhic alumina (Type 'H'; 50 g). The column was eluted with ethyl acetate (6 × 50 ml portions) and the eluate was evaporated to give the ether. This was crystallised from light petroleum (b.p 60°–80°) to give a white solid, m.p. 108°.

EXAMPLE 35

2-(2-Acetoxyethoxy)-5-[1-hydroxy-2-[(1-methyl-3-phenylpropyl)amino]ethyl]benzamide, hydrochloride a. 5(N,N-Dibenzylglycyl)-2-(2-acetoxyethoxy)benzamide A solution of 5-(N,N-dibenzylglycyl)-2-(2-hydroxyethoxy)-benzamide (see Example 6(a)) (2.5 g) in acetic anhydride (10 ml) and acetic acid (10 ml) was heated at 100° for 1.25 hours, cooled, and poured into water. After being allowed to stand for 2 days at room temperature the aqueous solution was basified with sodium bicarbonate and extracted with ethyl acetate (3 × 100 ml). The dried extract was evaporated and the ether-soluble portion of the residue treated with ethereal hydrogen chloride. The precipitate (1.6 g) in water (50 ml) was basified with sodium bicarbonate solution and was extracted with ether (3 × 50 ml). The dried extracts were evaporated to give a solid m.p. 120°–128° (from ethyl acetate).

b.

2-(2-Acetoxyethoxy)-5-[1-hydroxy-2-[(1-methyl-3-phenylpropyl)amino]ethyl]benzamide, hydrochloride Prepared from the above base (Example 35a) by catalytic hydrogenation in the presence of benzylacetone as described in Example 17(c).

The hydrochloride crystallised from methanol-ethyl acetate as colourless crystals, m.p. 146°–150°.

EXAMPLE 36

5-(2-tert-Butylamino-1-hydroxyethyl)-2-pentyloxy benzamide, hydrochloride

A mixture of 5-(2-tert-butylamino-1-hydroxyethyl) salicylamide, hydrochloride (8.7 g) and anhydrous potassium carbonate (8.25 g) in dimethylformamide (100 ml) were heated at 100° for 1 hour. 1-Bromopentane (4.5 g) in dimethylformamide (25 ml) was added and the mixture was heated at 100° for a further 2 hours. The solvent was removed and the residue was partitioned between water and ethyl acetate. The dried (MgSO$_4$) ethyl acetate solution was evaporated to yield a red oil which was chromatographed on alumina. Eluation with ethyl acetate gave the required benzamide which was obtained as a colourless oil which was converted into its hydrochloride (1.55 g) m.p. 162°–167°. Recrystallisation from ethyl acetate-methanol raised the m.p. to 169°–172°.

EXAMPLE 37

5-(2-tert-Butylamino-1-hydroxyethyl)-2-(2-ethoxyethoxy)-benzamide, hydrochloride A solution of 5-(2-tert-butylamino-hydroxyethyl)-salicylamide (4.3 g) in dimethylformamide (30 ml) was added dropwise to a stirred suspension of sodium hydride (0.48 g of a 60% dispersion in oil) in dimethylformamide (10 ml). When the evolution of hydrogen ceased, 2-ethoxyethyl-p-toluene sulphonate (4.2 g) was added and the solution was heated at 100° for 4 hours. Evaporation of the solvent gave a grey oil which was suspended in water and extracted with ethyl acetate. The extracts were dried (MgSO$_4$), concentrated and treated with ethereal hydrogen chloride to afford the hydrochloride salt as a white solid (2 g) m.p. 189° – 190° (from ethyl acetate-methanol).

EXAMPLE 38

2-(2-Hydroxyethoxy)-5-[1-hydroxy-2[(1-methyl-propyl)amino]-ethyl]benzamide, hydrochloride A solution of 5-(N,N-dibenzylglycyl)-2-(2-hydroxyethoxy)-benzamide (2.5 g) and butanone (1 ml) in ethanol (125 ml) was hydrogenated for 45 hours in the presence of 5% platinum oxide on carbon (0.5 g) and 10% palladium oxide on carbon (0.5 g). When uptake of hydrogen (ca. 600 ml) had ceased the catalysts and solvent were removed and the residual oil was purified by chromatography on alumina. The product was eluted with ethyl acetate-methanol (9:1) to give a colourless oil which formed a hydrochloride salt (1.06 g) m.p. 159.5°–163° (from ethyl acetate-methanol).

EXAMPLE 39

2-(2-Ethoxyethoxy)-5-[1-hydroxy-2-[(1,1-dimethyl-3-phenylpropyl)amino]ethyl]benzamide, hydrochloride, monohydrate A mixture of 5-bromoacetyl-2-(ethoxyethoxy)benzamide (1.2 g) and 1,1-dimethyl-3-phenylpropylamine (0.6 g) in ethanol (15 ml), containing triethylamine (0.5 ml), was heated under reflux for 16 hours. The solution was cooled and sodium borohydride (0.6 g) was added portion-wise with stirring. After 3 hours, the mixture was acidified with 3N hydrochloric acid, concentrated under reduced pressure and the residue partitioned between 5N sodium hydroxide and ethyl acetate. The organic phase was dried (MgSO$_4$) and evaporated and the residue was chromatographed on 20 × 20 cm preparative layer plates (Merck, Kieselgel 60F 254 2mm thick) using ethyl acetate-methanol (2:1) as the eluent. The slowest moving band (Rf 0.36) was separated and extracted with methanol (300 ml). The solvent was removed and the residue was dissolved in ethyl acetate-methanol and treated with ethereal hydrogen chloride to give the hydrochloride salt as a friable solid which foamed at 70°. Equiv. Wt. Found 473; required 469.

EXAMPLE 40

2-(2-Ethoxyethoxy)-5-[1-hydroxy-2-[1-(R)-(1-methyl-3-phenylpropyl)amino]ethyl]benzamide, hydrochloride a. 5-Bromoacetyl-2-(2-ethoxyethoxy)benzamide Bromine (1.168 g) in chloroform (10 ml) was added dropwise with stirring to a solution of 5-acetyl-(2-ethoxyethoxy)benzamide, (1.9 g) at such a rate as to minimise the amount of free bromine present. The solution was washed with water and 8% sodium bicarbonate solution, dried (MgSO$_4$) and evaporated to yield the bromo compound (1.9 g) m.p. 120.5°–121° (from methanol).

b.

2-(2-Ethoxyethoxy)-5-[1-hydroxy-2-[1-(R)-(1-methyl-3-phenylpropyl)-amino]ethyl]benzamide, hydrochloride dihydrate A solution of 5-bromoacetyl-2-(2-ethoxyethoxy)benzamide (0.99 g) and (R)-1-methyl-3-phenylpropylamine (0.45 g) (prepared according to the method of J. van Dijk et al, Rec. trav. chim., 82, 189 (1963)) in ethanol (100 ml) containing triethylamine (0.3 g) was heated under reflux for 4 hours. Sodium borohydride (1 g) was added and the mixture was stirred at room temperature for 0.5 hours. The solvent was evaporated and the residue was partitioned between ethyl acetate and 2N hydrochloric acid. The aqueous layer was basified with 2N sodium hydroxide and extracted with ethyl acetate. The latter extracts were dried (MgSO$_4$) and evaporated to dryness. The residue was washed with ether and then dissolved in ethyl acetate and treated with ethereal hydrogen chloride. The hydrochloride salt precipitated as a white solid (0.6 g) m.p. 85°–89°.

In a similar manner was prepared 2-(2-ethoxyethoxy)-5-[1-hydroxy-2-[1 - (S)-(1-methyl-3-phenylpropyl)amino]ethyl]-benzamide hydrochloride from the (S)-1-methyl-3-phenyl-propylamine. This compound was isolated as a monohydrate m.p. 85°–89° (from methanol-ethyl acetate).

EXAMPLE 41

2-(2-hydroxyethoxy)-5-(1-hydroxy-2[(3-[4-hydroxyphenyl]-1-methylpropyl)amino]ethyl)benzamide, hydrochloride, sesquihydrate A mixture of -5-(N,N-dibenzylglycyl)-2-(2-hydroxyethoxy)-benzamide (2 g) and 4-(4-hydroxyphenyl)-2-butanone (0.785 g) in ethanol (100 ml) and glacial acetic acid (0.5 ml) was hydrogenated in the presence of 5% platinum oxide on carbon (0.5 g) and 10% palladium oxide on carbon (0.5 g). The catalyst and solvent were removed and the residue was converted into the hydrochloride salt m.p. 75°-80° frothed (methanol-ethyl acetate).

EXAMPLE 42 a.
2-(2-Ethoxyethoxy)-5-[1-hydroxy-2-[(3-methoxy-1-methylpropyl)amino]ethyl]benzamide, hydrochloride A mixture of 5-(N,N-Dibenzylglycyl)-2-(2-ethoxyethoxy) benzamide (3.1 g), 4-methoxy-2-butanone (1.1 g), 5% platinum on charcoal (0.3 g) and 10% palladium on charcoal (0.5 g) in ethanol (75 ml.) was hydrogenated for 40 hours. The catalysts and the solvent were removed to leave the product as an oil, which was converted into its hydrochloride salt (2.0 g), m.p. 111°-116°. The salt was obtained as colourless needles from ethyl acetate-methanol, m.p. 122°-123°.

The following compounds were also prepared by a similar procedure from the appropriate ketone.

b. 2-(2-Ethoxyethoxy)-5-[2-[(3-ethoxy-1-methylpropyl)amino]-1-hydroxyethyl]benzamide, was obtained as its fumarate salt, hemihydrate, as a glass that foamed at 54°-57°.

c. 2-(2-Ethoxyethoxy)-5-[1-hydroxy-2-[(2-methoxy-1-methylethyl)amino]ethyl]benzamide, hydrochloride, m.p. 129°-132° (ethyl acetate-methanol).

d. 2-(2-Ethoxyethoxy)-5-[1-hydroxy-2-[(4-methoxy-1-methylbutyl)amino]ethyl]benzamide, hydrochloride, m.p. 141°-142°. (ethyl acetate-methanol).

EXAMPLE 43

5-[2-[3-(p-Acetamidophenyl)-1-methylpropyl]amino-1-hydroxyethyl]-2-(2-ethoxyethoxy) benzamide, hydrochloride.

A solution of 5-(N,N-dibenzylglycyl)-2-(2-ethoxyethoxy)-benzamide (4.46 g) and α-acetonyl-p-acetotoluidide (2.05 g) in ethanol (300 ml.) was treated with hydrogen, at atmospheric pressure and room temperature, in the presence of 5% platinum on charcoal (0.5 g.) and 10% palladium on charcoal (0.5 g.). The uptake of hydrogen was complete after 48 hours. The catalysts and solvent were removed to leave the product as an oil which was converted into its hydrochloride salt (3.5 g.), m.p. 85°-89°. Recrystallisation from methanol-ethyl acetate gave a colourless solid, m.p. 93°- 95°.

EXAMPLE 44

2-(2-Ethoxyethoxy)-5-[1-hydroxy-2[[1-methyl-3-[4(methane-sulphenamido)phenyl]propyl]amino]ethyl]benzamide, acetate (salt), monohydrate.

A solution of p-(3-oxobutyl)methanesulphonanilide (1.9 g) acetic acid (1 ml.) and 5-(N,N-dibenzylglycyl)-2-(2-ethoxyethoxy)benzamide (2.93 g) in ethanol (200 ml.) was added under nitrogen to a mixture of 10% palladium on charcoal (0.3 g) and 5% platinum on charcoal (0.3 g). The mixture was stirred under hydrogen at atmospheric pressure and room temperature for 48 hours. The catalysts and solvent were removed to leave a gum which solidified when it was triturated with dry ether to give the product (0.85 g), m.p. 53°-63°. Equivalent weight: found, 583, required 572.

The following Table sets out the activities of a representative number of the compounds described in the preceding Examples using the test described herein.

| Compound | $R_1$ | $R_2$ | $R_3$ | $R_4$ | $\beta_1$ Heart rate | $\beta_2$ Blood pressure |
|---|---|---|---|---|---|---|
| Propranolol | | | | —CH(ME)CH$_2$CH$_2$— | 1.0 | 1.0 |
| Example 3 of UK 1260521 | H | H | —Me | " | 3.8 | 3.8 |
| Example 8 of UK 1260521 | H | H | —CH$_2$—CH=CH$_2$ | " | 0.76 | 0.76 |

| | | $R_4$ | $R_5$ | $R_6$ | $R_7$ | $\beta_1$ | $\beta_2$ |
|---|---|---|---|---|---|---|---|
| Example | 1 | H | H | —(CH$_2$)$_4$Me | —CH(Me)CH$_2$CH$_2$—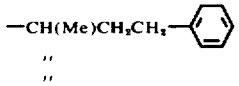 | 2.4 | >100 |
| " | 3 | H | H | —(CH$_2$)$_5$Me | " | 4.5 | >100 |
| " | 2 | H | H | —(CH$_2$)$_3$Me | " | 1.1 | >100 |
| " | 33 | H | H | —CH$_2$CH=CHCH$_3$ | " | 3 | 28 |
| " | 7 | H | H | —(CH$_2$)$_2$OMe | " | 7 | >100 |
| " | 8 | H | H | —(CH$_2$)$_3$OMe | " | 0.7 | >100 |
| " | 11 | H | H | —(CH$_2$)$_2$OBu$^n$ | " | 1.4 | >100 |
| " | 10 | H | H | —(CH$_2$)$_2$OPr$^i$ | " | 1 | >100 |
| " | 9 | H | H | —(CH$_2$)$_2$OPr$^n$ | " | 1.5 | >100 |

| Compound | | $R_4$ | $R_5$ | $R_6$ | $R_7$ | $\beta_1$ | $\beta_2$ |
|---|---|---|---|---|---|---|---|
| Example | 17 | H | H | —(CH$_2$)$_4$OH | —CH(Me)CH$_2$CH$_2$— | 3 | 75 |
| " | 35 | H | H | —(CH$_2$)$_2$OCOMe | " | 3.9 | >100 |
| " | 24 | H | H | —(CH$_2$)OEt | —CHMe$_2$ | 4.8 | 48 |

-continued

| | | | | | | | |
|---|---|---|---|---|---|---|---|
| " | 20 | H | H | " | —(CH₂)₃—⌬ | 4 | 29 |
| " | 23 | H | H | " | —CH(Me)(CH₂)₂—⌬(OMe)(OMe) | 5 | 90 |
| " | 30 | H | H | " | —CH₂CH(Me)CH₂—⌬ | 7 | >100 |
| " | 39 | H | H | " | —C(Me)₂CH₂CH₂—⌬ | 3 | 60 |
| " | 42(a) | H | H | " | —CH(Me)CH₂CH₂OMe | 2.4 | >100 |
| " | 31 | H | H | " | —CH(Me)Et | 2.6 | >100 |
| " | 42(b) | H | H | —(CH₂)₂OEt | —CH(Me)CH₂CH₂OEt | 4.3 | >100 |
| " | 27 | H | H | " | —CH(Me)CHME₂ | 13.5 | >100 |
| " | 42(c) | H | H | " | —CH(Me)CH₂OMe | 12.1 | >100 |
| " | 29 | H | H | " | —CH(Me)(CH₂)₂—⌬—OMe | 4.1 | >100 |
| " | 43 | H | H | " | —CH(Me)(CH₂)₂—⌬—NHCOCH₃ | 2.1 | >100 |
| " | 28 | H | H | " | —CH(Me)(CH₂)₂—⌬(OMe)(OH) | 0.9 | 31 |
| " | 42(d) | H | H | " | —CH(Me)(CH₂)₃OMe | 3 | >100 |

EXAMPLE 45 Pharmaceutical Compositions

Capsules

To prepare 10,000 capsules each containing 25 mg active ingredient.

Mix together 250 g powdered active ingredient with a sufficient quantity of microcrystalline cellulose B.P.C. and fill into No. 3 hard gelatin capsules so that each capsule contains about 120 mg of the mixture.

Capsules may be similarly prepared each containing 50 mg active ingredient.

Tablets

To prepare 5,000 tablets each containing 100 mg active ingredient.

Mix together 500 g active ingredient, 490 g microcrystalline cellulose B.P.C., 5 g magnesium stearate and 5 stearic acid B.P. Compress the powders on a suitable tabletting press to produce tablets each 6.5 mm in diameter and weighing about 200 mg.

To prepare 5,000 tablets each containing 200 mg active ingredient.

Mix together 1,000 g active ingredient, 500 g lactose and 175 g maize starch, and sufficient of a 2% aqueous solution of sodium hydroxymethyl cellulose to produce a damp cohesive mass. Pass the damp mass through a No. 13 mesh B.S.S. sieve and dry in a fluidised bed dryer at 60° C. Pass the dried granules through a No. 22 B.S.S. sieve and mix with 60 g dried maize starch and 15 g magnesium stearate. Compress the lubricated granules on a suitable tabletting press using 9.5 mm deep concave punches to produce tablets each weighing about 350 mg. These tablets may be film coated with a suitable film forming material such as methyl cellulose, hydroxypropyl methyl cellulose or mixtures of these materials using standard techniques. The tablets may also be sugar coated by the standard sugar coating techniques.

Injection

To prepare an injection containing 10 mg active ingredient per ml.

Dissolve 10 g active ingredient and 7.5 g sodium chloride in 950 ml water for injections. When solution is complete make up to 1 liter with more water for injections. Subdivide the solution into suitable size ampoules (1 ml, 5 ml or 10 ml) seal and sterilise by heating in an autoclave.

The active ingredient is the compound of Example 19 although this can be replaced by any other compound according to the invention if desired.

We claim:

1. A compound of the formula

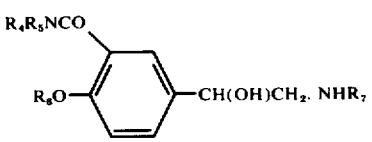

in which $R_4$ and $R_5$ independently represent hydrogen or lower alkyl; $R_6$ represents a straight or branched alkyl or alkenyl group containing from 4 to 6 carbon atoms, inclusive, or $R_6$ represents a straight or branched alkyl group containing from 2 to 6 carbon atoms, inclusive, which alkyl group is substituted by one or more hydroxy, alkoxy or acyloxy groups; or by an aryl group which may be substituted by one or more hydroxy, alkoxy or acyloxy groups as before; and $R_7$ represents a straight or branched alkyl group containing from 3 to 6 carbon atoms, inclusive, optionally substituted by an aryl substituted with hydroxy, alkoxy, acetamido or methanesulphonamido groups; or optionally substituted by an alkoxy group or aryloxy group which, alkoxy or aryloxy group may, in turn, be substituted by hydroxy, alkoxy, acetamido or methanesulphonamido groups, and pharmaceutically acceptable salts thereof.

2. A compound as claimed in claim 1 in which $R_4$ and $R_5$ are hydrogen.

3. A compound as claimed in claim 1 in which $R_6$ represents one of the following groups: $C_{4-6}$ alkyl, dihydroxyalkyl, hydroxyalkyl, alkoxyalkyl, acyloxyalkyl, aralkyl, hydroxyaralkyl, alkoxyaralkyl, acyloxyaralkyl, or alkenyl.

4. A compound as claimed in claim 1 in which $R_7$ represents alkyl, alkoxyalkyl, hydroxyaralkyl, mono and dialkoxyaralkyl, alkoxyhydroxyaralkyl acetamidoaralkyl, sulphonamidoaralkyl, aryloxyalkyl.

5. The compound of claim 1 which is 2-(2-ethoxyethoxy)-5-[1-hydroxy -2-[[3-(4-hydroxyphenyl)-1-methylpropyl]amino]ethyl]benzamide, hydrochloride.

6. The compound of claim 1 which is 2-(2-ethoxyethoxy)-5-[1-hydroxy-2[(3-methoxy-1-methylpropyl)amino]ethyl]benzamide, hydrochloride.

7. The compound of claim 1 which is 5-[2-[3-(4-acetamidophenyl)-1-methylpropyl]amino-1-hydroxyethyl]-2-(2-ethoxyethoxy)benzamide, hydrochloride.

8. The compound of claim 1 which is 2-(ethoxyethoxy)-5-[1-hydroxy-2[[3-(4-hydroxy-3-methoxyphenyl)-1-methylpropyl]-amino]ethyl]benzamide, hydrochloride.

9. The compound of claim 1 which is 2-(2-hydroxyethoxy)-5-(1-hydroxy-2[(3-[4-hydroxyphenyl]-1-methylpropyl)amino]ethyl)benzamide, hydrochloride, sesquihydrate.

* * * * *